US00PP36050P2

(12) United States Plant Patent
Hung et al.

(10) Patent No.: US PP36,050 P2
(45) Date of Patent: Jul. 30, 2024

(54) ***HOMALOMENA* PLANT NAMED "HUTAHM06"**

(50) Latin Name: *Homalomena rubescens*
Varietal Denomination: HUTAHM06

(71) Applicant: Huta Green Company Limited, Hanoi (VN)

(72) Inventors: Pham Ngoc Hung, Hiep Cuong Commune (VN); Le Tuan Anh, Thai Binh (VN)

(73) Assignee: Huta Green Company Limited, Hanoi (VN)

( * ) Notice: Subject to any disclaimer, the term of this patent is extended or adjusted under 35 U.S.C. 154(b) by 0 days.

(21) Appl. No.: 18/445,563

(22) Filed: Oct. 18, 2023

(51) Int. Cl.
*A01H 5/02* (2018.01)
*A01H 6/10* (2018.01)

(52) U.S. Cl.
USPC ..... Plt./263.1

(58) Field of Classification Search
USPC ..... Plt./263.1
See application file for complete search history.

*Primary Examiner* — Karen M Redden
(74) *Attorney, Agent, or Firm* — Samuel R. McCoy, Jr.

(57) ABSTRACT

'HUTAHM06' is a new and distinctive *Homalomena* plant which is characterized by a compact, upright growth habit with uniquely variegated foliage borne on long, greyed-red petioles and the stability of all characteristics from generation to generation. The new variety is typically produced as an indoor ornamental plant.

5 Drawing Sheets

Latin name of the genus and species: The Latin name of the genus and species of the novel variety disclosed herein is *Homalomena rubescens.*

Variety denomination: The inventive variety of *Homalomena* disclosed herein has been given the variety denomination 'HUTAHM06'.

BACKGROUND OF THE INVENTION

Parentage: The claimed plant originated as a Ethyl methanesulfonate-induced, whole-plant mutation of an unnamed, red-stemmed *Homalomena rubescens*. In the spring of 2019, meristematic tissue culture propagation of said red-stemmed *Homalomena rubescens* plant was initiated at a plant tissue culture laboratory in Hanoi, Vietnam. After five months in culture, the plant tissue was transferred to an agar medium to induce multiplication of meristematic plant tissue. After one month, the plant tissue was treated with Ethyl methanesulfonate in order to induce mutation. Once these plant tissue cultures had developed juvenile leaf shoots and calluses, they were transferred to a soilless growing media and acclimatized in a greenhouse. This process resulted in approximately 5000 rooted young plants. Said plants were grown to the 4-leaf stage, at which point any plantlets exhibiting variation in leaf color, variation in leaf shape, or leaf variegation were isolated. In February of 2020, after evaluating said isolated plants, one plant was observed to exhibit unique foliage variegation relative to all other candidate plants resulting from the induced-mutation. The plant was isolated and further evaluated to confirm the characteristics first observed. In January of 2022, it was determined that the unique foliage variegation and coloration of the claimed plant would prove favorable for commercial marketability.

Asexual Reproduction: Asexual reproduction of 'HUTAHM06', by way of meristematic tissue culture propagation, was first performed in 2022 at a plant tissue culture laboratory in Hanoi, Vietnam. Three successive generations so produced have shown that the unique features of the instant cultivar are stable and reproduced true to type.

SUMMARY OF THE INVENTION

The cultivar 'HUTAHM06' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Homalomena* cultivar 'HUTAHM06'. These traits, in combination, distinguish 'HUTAHM06' as a new and distinct cultivar.

1. *Homalomena* 'HUTAHM06' exhibits a compact, upright growth habit; and
2. *Homalomena* 'HUTAHM06' exhibits variegated cordate foliage borne on relatively long, greyed-red petioles; and
3. *Homalomena* 'HUTAHM06' exhibits conspicuously variegated foliage that varies from leaf to leaf with some laminas being nearly solid green-yellow with a small amount of dark green and greyed-green flecking, to others nearly solid green-yellow with large dark green and greyed-green blotches covering a relatively large portion of the lamina, to still other laminas exhibiting a homogenous mix of green-yellow at and near the midrib and lateral veins with fine flecking with the balance of the lamina exhibiting dark green, mid green, and light greyed-green flecks, blotches and streaks.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
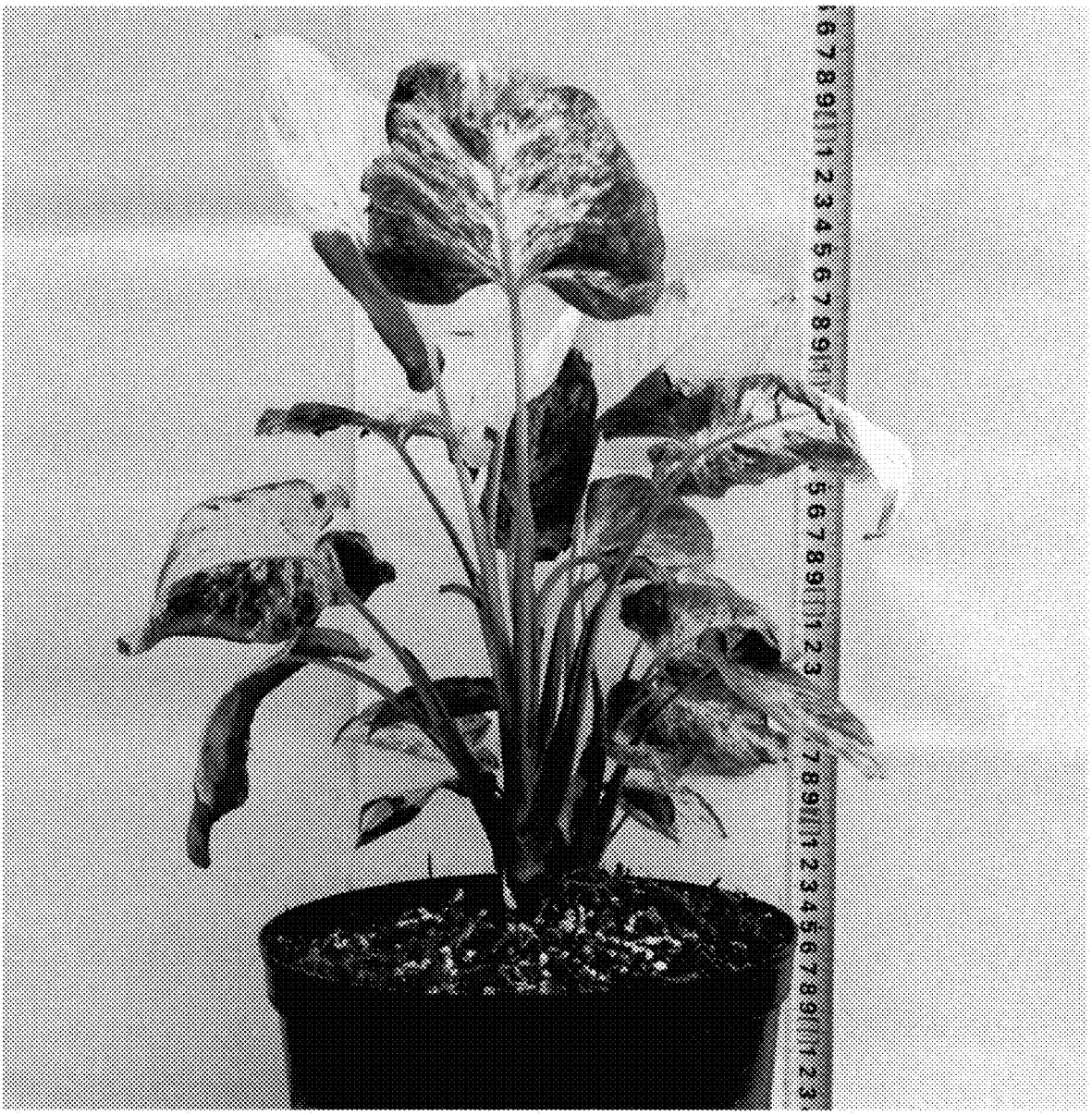
FIG. 1 illustrates an exemplary plant of the new cultivar, 'HUTAHM06', in profile. The plant shown is approximately 4 months old from a rooted cutting, potted into a 15 cm nursery container, grown in a greenhouse in Hanoi, Vietnam.
Figure 2:
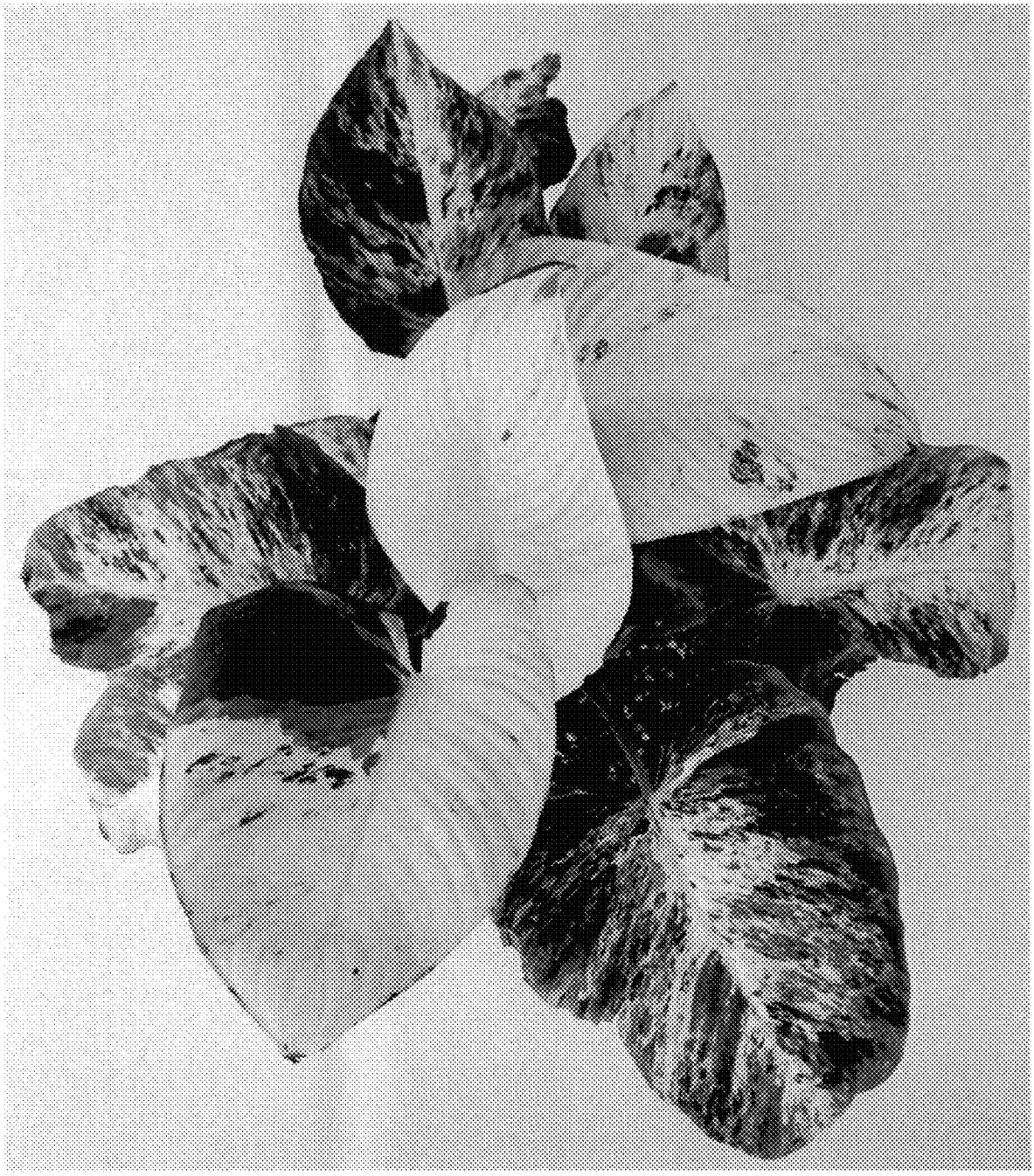
FIG. 2 illustrates an aerial perspective of the claimed plant, showing the typical foliar variegation.
Figure 3:
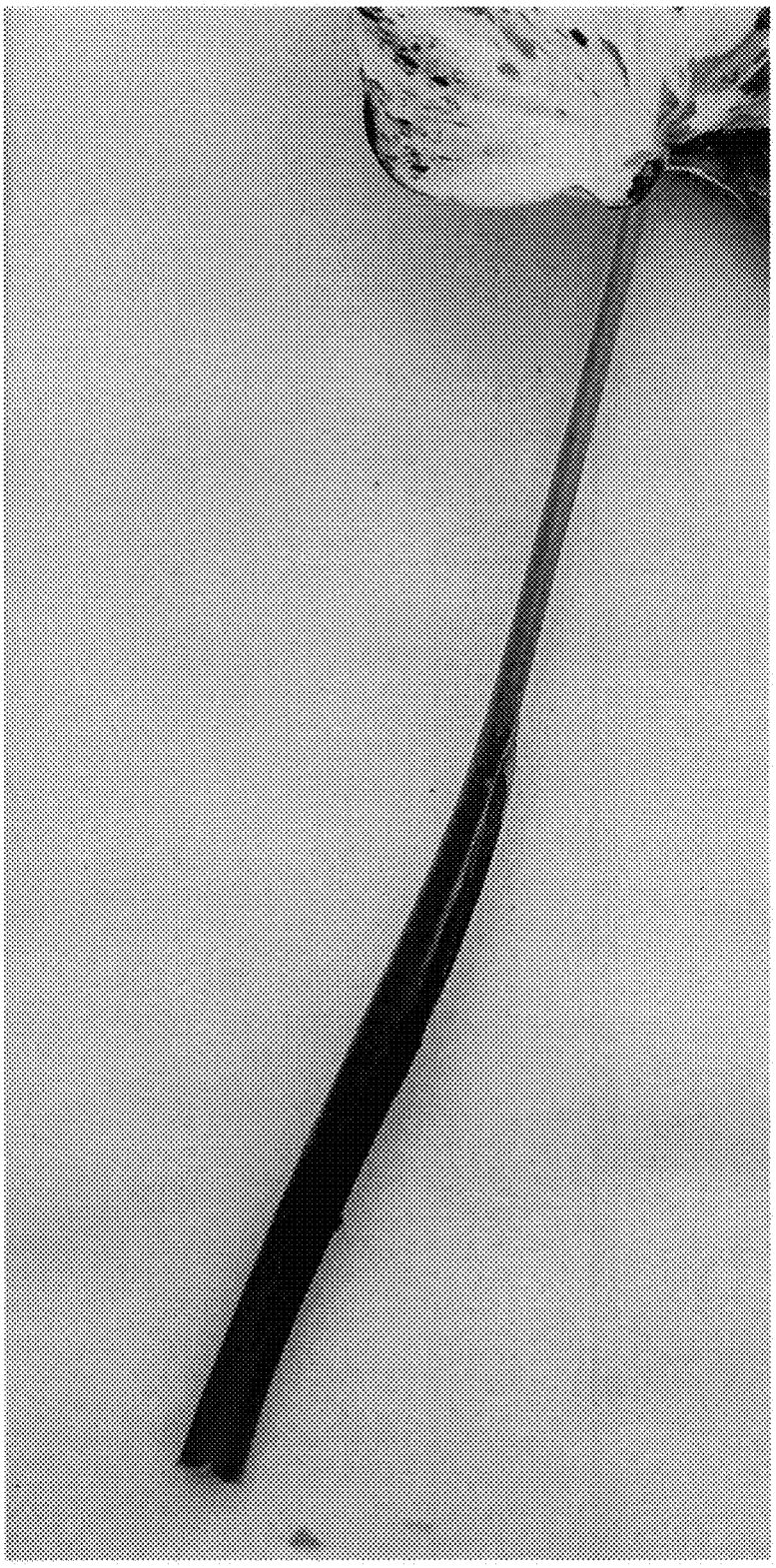
FIG. 3 illustrates the mature petiole of 'HUTAHM06'.
Figure 4:
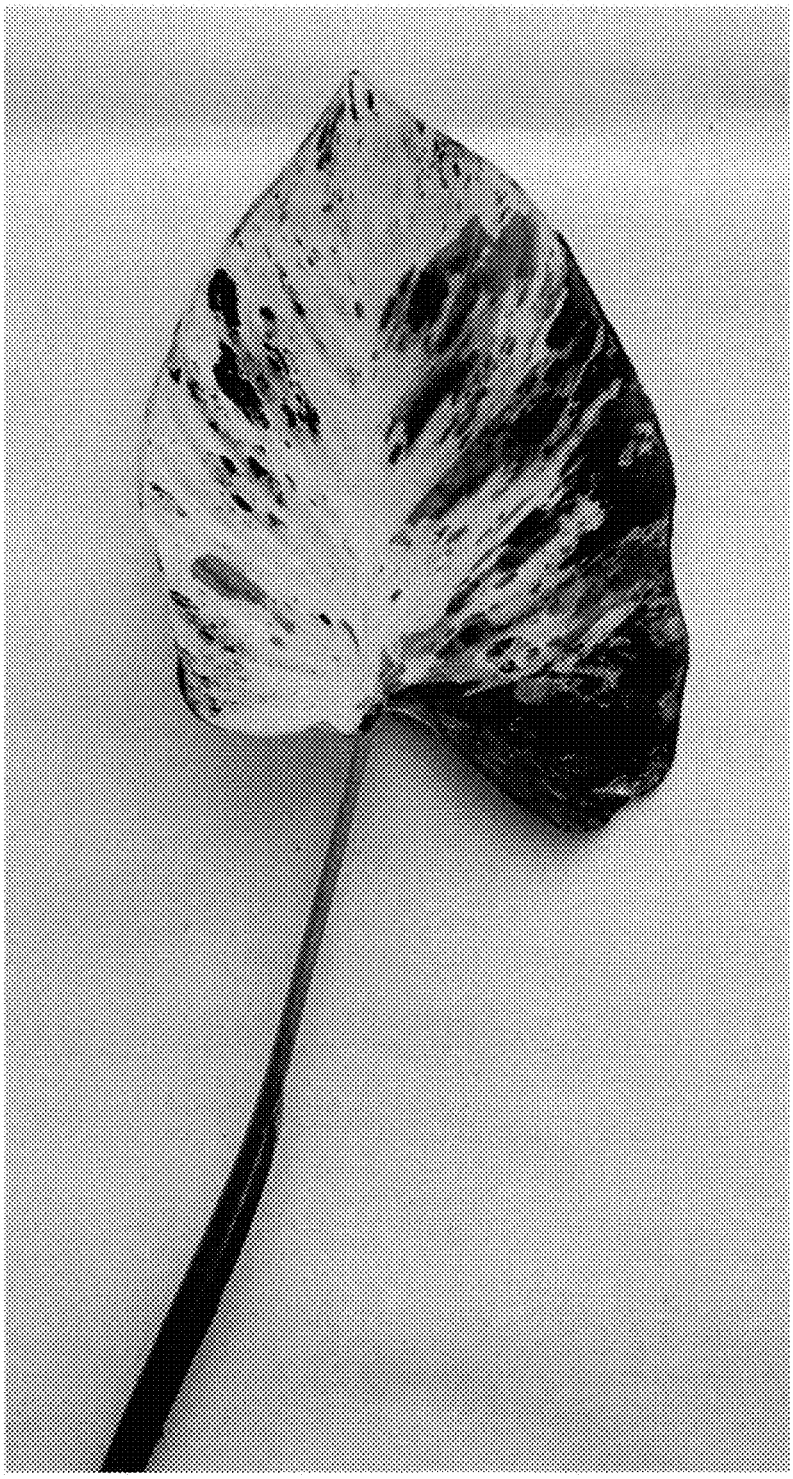
FIG. 4 illustrates the adaxial surface of the mature foliage of 'HUTAHM06'.
Figure 5:
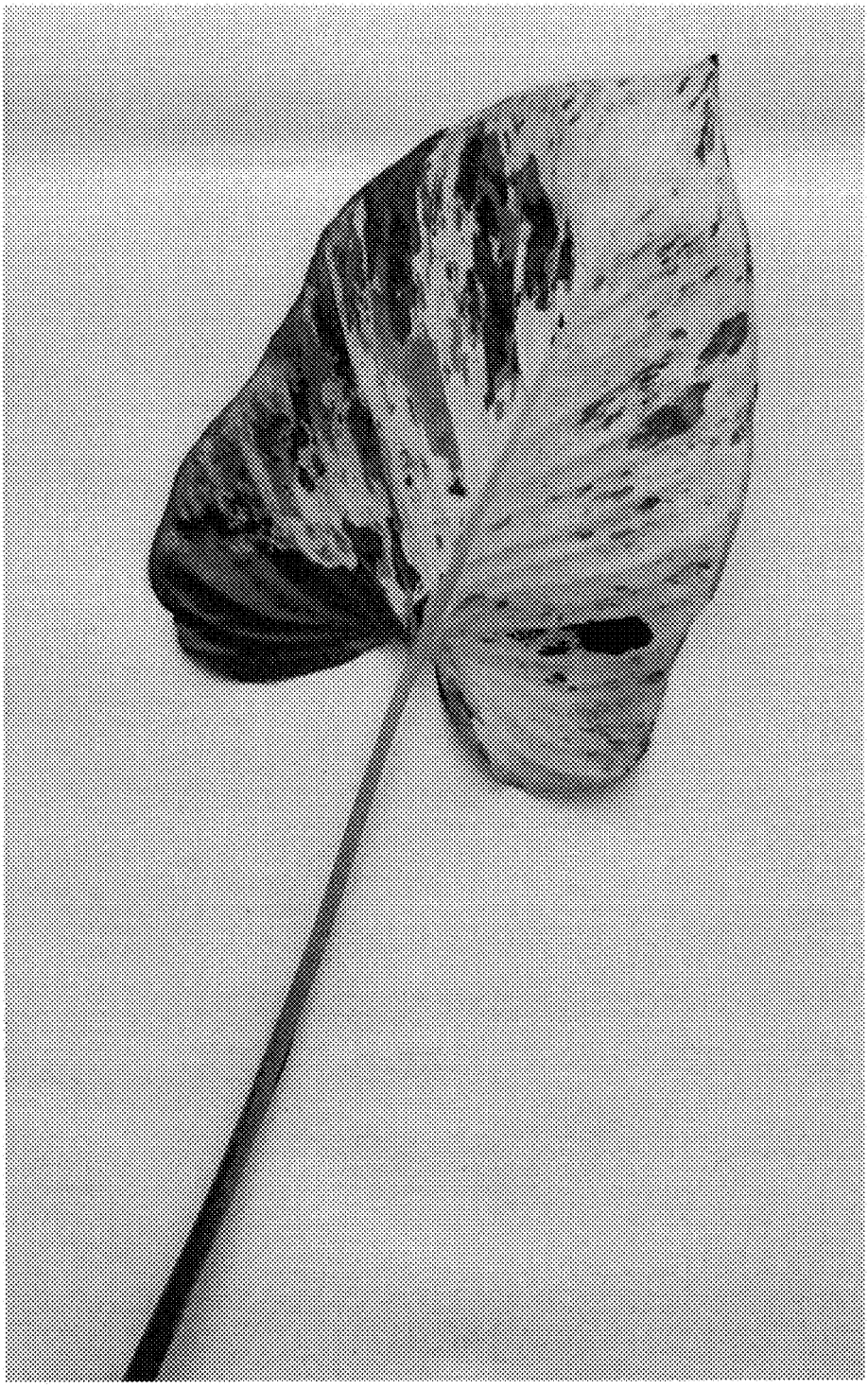
FIG. 5 illustrates the abaxial surface of the mature foliage of 'HUTAHM06'.

The following observations and measurements made in October of 2023 describe a 4-month-old 'HUTAHM06' plant grown in a 15 cm nursery container at commercial greenhouse in Hanoi, Vietnam. Plants were produced using conventional greenhouse production protocols for *Homalomena* species which consisted of overhead irrigation twice a week, weekly applications of a liquid 20-20-20 fertilizer at an electroconductivity of 0.8, and anti-bacteria oxalinic acid at a rate of 375 parts-per-million and Imidacloprid insecticide at a rate 100 parts-per-million applied every two weeks. Plants were grown under shade (ranging from 5,000 to 15,000 lux) with ambient temperatures ranging from 20 to 35 degrees Celsius and humidity levels ranging from 70 to 80 percent.

Those skilled in the art will appreciate that certain characteristics will vary with older or, conversely, with younger plants. 'HUTAHM06' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on *The Royal Horticultural Society Colour Chart*, The Royal Horticultural Society, London, 1986 (third edition).

A botanical description of 'HUTAHM06' and comparisons with the parent and the most similar variety of common knowledge are provided below.

General plant description:

*Growth habit*.—Monopodial evergreen perennial, developing multiple shoots from rhizomes as plants age; individual shoots will develop an unbranched stem with age though none have been observed on the claimed plant.

*Plant profile*.—Upright, globular.

*Height*.—35 cm to the top of the floral plane.

*Width*.—25 cm.

*Plant vigor*.—Vigorous.

*Propagation*.—Method — Meristematic tissue culture. Time to initiate roots — Approximately 24 weeks to initiate roots at an average ambient temperature of 25 degrees Celsius. Crop time — Approximately 16 weeks to produce a well-rooted, marketable 20 cm container from a rooted cutting.

*Environmental tolerances*.—Moderately high tolerance to rain; low to moderate tolerance to wind; not drought tolerant; tolerant of temperatures to at least 35 degrees Celsius. Cold hardy to USDA Hardiness Zone 10.

*Pest resistance and susceptibility*.— Plants have not been observed to be any more or less susceptible or resistant to pathogens and pests common to *Homalomena* sp.

Root system:

*General*.—Rhizomatous and bearing a freely-branching, moderately dense network of fleshy roots which are distributed from shallow to moderately deep within the soil profile.

Foliage:

*Arrangement*.—Alternate to spiraled.

*Division*.—Simple.

*Attachment*.—Petiolate.

*Quantity of leaves per shoot*.—14 on the oldest shoot.

*Quantity of shoots per plant*.—3.

*Quantity of leaves per plant*.—Approximately 28.

*Lamina*.—Shape — Cordate. Apex — Broadly acuminate. Base — Cordate. Aspect — Convex with the apex curling downward. Attitude — Outward to somewhat pendulous. Dimensions — 17.5 cm long and 12.5 cm wide, at the widest point. Margin — Entire; moderately, coarsely undulating. Texture and luster, adaxial surface — Lightly to moderately rugose, glabrous, and moderately glossy. Texture and luster, abaxial surface — Lightly to moderately rugose, glabrous, and slightly glossy to matte. Juvenile color, adaxial and abaxial surfaces — A relatively small portion of the lamina along the midrib and radiating a short distance away from the midrib, along the lateral veins, is green-yellow, nearest to RHS 1B,; green-yellow portions are finely and irregularly flecked, streaked, and blotched with a combination dark green and light greyed-green, nearest to RHS 139A, 137B, and 191B, respectively; the balance of the lamina is a homogenous combination of relatively large dark green, mid green, and light greyed-green flecks, blotches and streak, nearest to RHS 139A, 137B, and 191B, respectively. Mature color, adaxial and abaxial surfaces — Variable, with some laminas being nearly solid green-yellow (nearest to RHS 1C) with a small amount of dark green and greyed-green flecking (nearest to RHS 139A and 191B, respectively), to others nearly solid green-yellow (nearest to RHS 1C) with large dark green and greyed-green blotches covering a relatively large portion of the lamina, bounded by lateral veins (nearest to RHS 139A and 191B, respectively), to still other laminas exhibiting a homogenous mix of green-yellow (nearest to RHS 1C) at and near the midrib and lateral veins with fine flecking with the balance of the lamina exhibiting dark green, mid green, and light greyed-green flecks, blotches and streak (RHS 139A, 137B, and 191B). Venation — Vein pattern — Pinnate. Vein color, adaxial surface — The main vein and lateral veins are indistinguishable from the surrounding laminar surface. Vein color, abaxial surface — The main vein is yellow-green, nearest RHS 145A at, proximally, and fades lighter until it becomes indistinguishable from the surrounding laminar surface at about twothirds of the way to the apex; all lateral veins are indistinguishable from the surrounding laminar surface.

*Petiole*.—Attachment — Sheathed. Aspect — Terete. Length — Approximately 21.5 cm. Width — Approximately 1.0 cm, including the petiole wings, at the proximal end and 0.4 cm at the distal end. Strength — Moderately strong. Texture — Verrucose; glabrous. Luster — Matte to very slightly glossy. Color, adaxial and abaxial surfaces — Juvenile petioles are greyed-red, RHS 182B, and lightly to moderately suffused with yellow-green, nearest to in between RHS 146A and 148A; mature petioles are dark greyed-red at the base, nearest to RHS 181A, becoming lighter greyed-red with yellow-green suffusion towards the lamina, nearest to RHS 181C with 145A, respectively; yellow-green, distally, nearest to RHS 145A. Petiole wings — General Description — Two petiole wings are present at the base of each petiole. Length — Approximately 12.8 cm on mature petioles. Width — Approximately 0.4 cm at the base on mature petioles. Margins — Entire; very light, coarse undulation. Texture and luster — Glabrous and very slightly glossy. Color, juvenile — Emerging yellow-green, nearest to RHS 144A, with broad green margins, RHS 143A; aging to yellow-green, RHS 145C, with moderate to heavy greyed-red suffusion, RHS 182B. Color, mature — Nearest to a mixture of greyed-orange and greyed-purple, RHS 166A and 183A, and occasionally margined with lighter greyed-purple, nearest to RHS 184A.

Inflorescence: *Homalomena deliciosa* typically produces a spathe and spadix inflorescence, but no flowering of the claimed plant has been observed to date.

Flower buds: No flowering has been observed to date.

Flowers: No flowering has been observed to date.

Reproductive organs: No flowering has been observed to date.

Seed and fruit: No flowering has been observed to date.

COMPARISONS WITH THE PARENT

Plants of the new cultivar 'HUTAHM06' may be distinguished from the parent, an unnamed red-stemmed *Homalomena rubescens* plant (not patented), by the characteristics described in Table 1.

TABLE 1

| Characteristic | 'HUTAHM06' | The parent. |
|---|---|---|
| Foliage luster. | Less glossy than the parent. | Glossier than 'HUTAHM06'. |
| Mature foliage coloration. | Variegated foliage; some laminas are nearly solid green-yellow with a small amount of dark green and greyed-green flecking; others are nearly solid green-yellow with large dark green and greyed-green blotches covering a relatively large portion of the lamina; other laminas exhibit a homogenous mix of green-yellow at and near the midrib and lateral veins with fine flecking with the balance of the lamina exhibiting dark green, mid green, and light greyed-green flecks, blotches and streaks. | Not variegated; solid dark green. |

COMPARISONS WITH THE MOST SIMILAR COMMERCIAL VARIETY

Plants of the new cultivar 'HUTAHM06' may be distinguished from the most similar commercial comparator known to the inventor, *Homalomena rubescens* 'Variegata' (not patented), by the characteristics described in Table 2.

TABLE 2

| Characteristic | 'HUTAHM06' | 'Variegata' |
|---|---|---|
| Foliage apex. | Broadly acuminate. | Cuspidate to near obtuse. |
| Foliage aspect. | Convex with the apex curling downward. | Near flat with revolute margins. |
| Expression of the foliar color patterns; adaxial and abaxial surfaces. | Varying from leaf to leaf with some laminas being nearly solid green-yellow with a small amount of dark green and greyed-green flecking, to others nearly solid green-yellow with large dark green and greyed-green blotches covering a relatively large portion of the lamina, to still other laminas exhibiting a homogenous mix of green-yellow at and near the midrib and lateral veins with fine flecking with the balance of the lamina exhibiting dark green, mid green, and light greyed-green flecks, blotches and streaks. | Irregularly flecked and blotched with cream white; additionally, some areas of the laminar occasionally exhibit epidermal blistering which appears as translucent-white blotches, typically bounded by lateral veins, revealing flecks and blotches beneath; blisters occasionally lightly suffused with yellow-orange or red-orange. |

That which is claimed is:

1. A new and distinct variety of *Homalomena rubescens* plant named 'HUTAHM06', substantially as described and illustrated herein.

* * * * *